US007119261B1

(12) United States Patent
Schaffer

(10) Patent No.: US 7,119,261 B1
(45) Date of Patent: Oct. 10, 2006

(54) METHOD FOR BREEDING TOMATOES HAVING REDUCED WATER CONTENT AND PRODUCT OF THE METHOD

(75) Inventor: Arthur Schaffer, Hashmonaim (IL)

(73) Assignee: The State of Israel-Ministry of Agriculture & Rural Development, Beit-Dagan (IL)

( * ) Notice: Subject to any disclaimer, the term of this patent is extended or adjusted under 35 U.S.C. 154(b) by 206 days.

(21) Appl. No.: 10/069,389

(22) PCT Filed: Jul. 4, 2000

(86) PCT No.: PCT/IL00/00389

§ 371 (c)(1),
(2), (4) Date: Jun. 27, 2002

(87) PCT Pub. No.: WO01/13708

PCT Pub. Date: Mar. 1, 2001

(30) Foreign Application Priority Data

Aug. 19, 1999 (IL) ..................... 131509

(51) Int. Cl.
*A01H 5/00* (2006.01)
*A01H 1/00* (2006.01)
*A01H 1/02* (2006.01)
*A01H 5/08* (2006.01)

(52) U.S. Cl. .................... 800/317.4; 800/269; 800/260
(58) Field of Classification Search ............ 800/317.4, 800/260, 263, 269, 277, 278; 435/423; 536/23.6
See application file for complete search history.

(56) References Cited

U.S. PATENT DOCUMENTS 5,817,913 A * 10/1998 Schaffer ..................... 800/263

FOREIGN PATENT DOCUMENTS

WO    WO-00/05390 A2    2/2000

OTHER PUBLICATIONS

Davies, J. Nature 209 (5023): 640-641 (Feb. 1966).*
Azanza, F. et al. Theoretical and Applied Genetics 87: 965-972 (1994).*
Tanksley, S. et al. Theoretical and Applied Genetics 92: 213-224 (1996).*
Yousef, G. and Juvik, J. Theoretical and Applied Genetics 103: 1022-1027 (2001).*
Eshed, Y. and Zamir, D. Theoretical and Applied Genetics 88: 891-897 (1994).*
Azanza, F. et al. Theoretical and Applied Genetics 91:495-504 (1995).*
Eshed et al. Theor. Appl. Genet. 88: 891-897 (1994).*
Eshed et al. Genetics 141: 1147-1162 (1995).*
Frary et al. Theor. Appl. Genet. 108: 485-496 (2004).*
Tomato Genetics Cooperative Report, No. 54, pp. 1, 52, and 62; University of Florida: Bradenton. (Sep. 2004).*
Nesbitt et al. 2002. Genetics 162: 365-379.*
Davis J.N., et al., "G.E. 1981. The constituents of tomato fruit—the influence of environment, nutrition and genotype." CRC Critical Reviews in Food Sci and Nutri. 15:205-280.
Grierson et al., 1986. "Fruit ripening and quality." In: Atherton, J.G. and Rudich, J. Eds.: Tomato Crop. Chapman and Hall, London, pp. 241-280.
R.J.L. and Scott, G.L., 1957. "The physical factors involved in the drying of Sultana grapes", Australian Journal of Agricultural Research, 8:444-459.
Nury, F.S. et al., 1973 "Fruits" In: Van Arsdel, W.B. Copley M.J. and Morgan, A.I., Eds.: Food Dehydration, Avi Publishing Co., Wesport, Conn., vol. 2, pp. 158-198.
Baker, E.A., et al, 1982. Composition of tomato fruit cuticles as related to fruit growth and development. In: Culter, D.F., Alvin, K.L. and Price, C.E., Eds.: The Plant Cuticle. Academic Press, London, pp. 33-44.
Ojimelukwe, P.C., 1994, "Effects of processing methods on absorbic acid retention and sensory characteristics of tomato products", J. Food Sci. Technol. 31:247-148.
Schaffer, A.A., et al., 1999, Modification of carbohydrate content in developing tomato fruit, Hortscience 34:12-14.
Bernacchi D., et al., 1998, Advanced backcross QTL analysis in tomato. Identification of QTLs for traits of agronomic importance from *Lycopersicon hirsutum*. Theor. Appl. Genet. 97:381-397.
Keith Hyde (edited), "The New Rural Industries, A Handbook for Farmers and Investors", Published Dec. 1997.
D. Bernacchi et al., "Advanced backcross QTL analysis of tomato. II. Evaluation of near-isogenic Lines carryign single-donar intnrogressions for desirable wild QTL-alleles derived from *Lycopersicon hirsutum* and *L. pimplnelilfolium*", Theor. Appl. Genet. (1998) 97:170-180; (1998) 97-1191-1196.

(Continued)

Primary Examiner—David T. Fox
Assistant Examiner—Keith O. Robinson

(57) ABSTRACT

A method for breeding tomato plants that produce tomatoes with reduced fruit water content including the steps of crossing at least one *Lycopersicon esculentum* plant with a *Lycopersicon* spp. to produce hybrid seed, collecting the first generation of hybrid seeds, growing plants from the first generation of hybrid seeds, pollinating the plants of the most recent hybrid generation, collecting the seeds produced by the most recent hybrid generation, growing plants from the seeds of the most recent hybrid generation, allowing plants to remain on the vine past the point of normal ripening, and screening for reduced fruit water content as indicated by extended preservation of the ripe fruit and wrinkling of the fruit skin.

5 Claims, No Drawings

OTHER PUBLICATIONS

Solanaceae Genomics Network (SGN) Data Overview, (www.sgn.cornell.edu/cgi-bin/content/sgn_data.pl).

Yuval Eshed and Dani Zamir, "An Introgression Line Population of *Lycopersicon pennelilli* in the Cultivated Tomato Enables the Identification and Fine Mapping of Yield-Associated QTL", Genetics 141:1147-1162 (Nov. 1995).

Yuval Eshed and Dani Zamir, "A genomic library of *Lycopersicon pennelilli* in *L. esculentum*: A tool for fine mapping of genes", Euphytica 79:175-179, published 1994.

Photgraphs of IL 4-4 tomatoes.

Lindsay Bareham, "The Big Red Book of Tomatoes" published Jun. 24, 1999.

* cited by examiner

METHOD FOR BREEDING TOMATOES HAVING REDUCED WATER CONTENT AND PRODUCT OF THE METHOD

FIELD OF THE INVENTION

The present invention relates to a method for breeding tomatoes having reduced water content and/or with the trait of drying while still attached to the vine, and to tomatoes having reduced water content and to products of the method.

BACKGROUND OF THE INVENTION

Dehydrated tomato products comprise an important portion of the tomato industry. The production of tomato pastes, ketchup and other processed tomato products is dependent on the energy-requiring steps of dehydration. The production of "sun-dried" tomato products consists of dehydrating cut tomato fruit either in the sun or in drying ovens.

Dry matter content of mature tomato fruit can range from approximately 5–10% (Davies, J. N. and Hobson, G. E. 1981. The constituents of tomato fruit—the influence of environment, nutrition and genotype. CRC Critical Reviews in Food Sci and Nutr. 15:205–280), depending largely on fruit size. Generally, processing tomato cultivars produce mature fruit with a higher water content of approximately approximate 94–95%. Smaller, "cherry"-type tomato fruit, with a fresh weight of 10–20 grams frequently have higher concentration of solids (dry weight) and hence reduced water concentrations of approximately 90% (10% dry weight).

Generally, tomato fruit development stages can be classified as the pre-climacteric stage, which is comprised of the early stages of fruit growth until incipient ripening, the climacteric stage and the post-climacteric or senescent stage. Once the fruit is fully ripe, tissue disorganization occurs, with pathogens contributing to the tissue disorganization, and characteristics associated with "overripening" and subsequent rotting of the fruit become apparent (Grierson, D. and Kader, A. A. 1986. Fruit ripening and quality. In: Atherton, J. G. and Rudich, J. Eds.: The Tomato Crop. Chapman and Hall, London, pp. 241–280).

The production of raisins from grape berries (*Vitis vinifera*) is a well known process in which the dehydration process occurs by diffusion of water through a waxy cuticle (Martin, R. J. L. and Scott, G. L. 1957. The physical factors involved in the drying of Sultana groups. Australian Journal of Agricultural Research. 8:444–459). For whole grape berries, the drying process is generally assisted by various dipping treatments of the berry, such as the soda-dip method (Nury, F. S., Brekke, J. E. and Bolin, H. R. 1973. Fruits. In: Van Arsdel, W. B., Copley, M. J. and Morgan, A. I., Eds: Food Dehydration. Avi Publishing Co., Westport, Conn. vol. 2, pp. 158–198). In brief, in this method the berries are dipped in a 0.2–0.3% solution of caustic soda (sodium hydroxide) at a temperature, of about 200° F. for a few seconds and are then rinsed with cold water before dehydration. The purpose of the dipping is to modify the berry cuticle so that transpiration of water vapor across the cuticle may proceed at a faster rate.

The tomato, like the grape, is botanically classified as a berry and has a waxy cuticle on the fruit epidermis (Baker, E. A., Bukovac, M. J. and Hunt, G. M. 1982. Composition of tomato fruit cuticles as related to fruit growth and development. In: Cutler, D. F., and Alvin, K. L. and Price, C. E., Eds: The Plant Cuticle. Academic Press, London, pp. 33–44). However, tomatoes will generally undergo degradation if they remain on the vine after ripening. In the case of tomatoes, the harvested fruit is generally cut in half in order to increase the dehydration rate. Alternatively, whole fruit may be pierced in order to facilitate fluid movement (Ojimelukwe, P. C. 1994. Effects of processing methods on ascorbic acid retention and sensory characteristics of tomato products. J. Food Sci. Technol. 31:247–248). Drying of the slices of pierced tomato fruit may take place either in the sun or in various forms of drying ovens based on non-solar energy input.

There are disadvantages to sun-drying since it depends on weather conditions and inclement weather leads to losses. Similarly, there are disadvantages to the use of drying ovens as these are energy consuming. Both sun drying and oven drying may lead to losses in food quality. For example, levels of ascorbic acid, one of the major nutritional contributions of tomatoes in the human diet, decrease significantly in response to sun-drying or oven-drying (Ojimelukwe, P. C. 1994. Effects of processing methods on ascorbic acid retention and sensory characteristics of tomato products. J. Food Sci. Technol. 31:247–248). Furthermore, the necessity to cut the tomato fruit in half before the drying process does not allow for the production of whole dried tomato fruit.

Wild species of the genus *Lycopersicon*, such as *L. hirsutum*, may contain within their genetic makeup expressed characteristics not generally present within the *L. esculentum* species. These genetic traits may be transferred to the cultivated *L. esculentum*. For example, the genetic trait of sucrose accumulation is present in mature fruit of the subgenus *Eriopersicon* (including *L. hirsutum*, *L. chmiliewskii* and *L. peruvianum*) and this trait has been transferred to *L. esculentum*, using classical genetic breeding techniques, as well as molecular genetic techniques (Schaffer, A. A., Petreikov, M., Miron, D., Fogelman, M., Spiegelman, M., Bnei-Moshe, Z., Shen, S., Granot, D., Hadas, R., Dai, N., Levin, I., Bar, M., Friedman, M., Pilowsky, M., Gilboa, N. and Chen, L. 1999. Modification of carbohydrate content in developing tomato fruit. Hortscience 34:12–14). The wild species of *Lycopersicon*, however, may also serve as a source of unexpressed genetic traits that can contribute to the value of cultivated plants (Bernacchi, D., Beck-Bunn, T., Eshed, Y., Lopez, J., Petiard, V., Uhlig, J., Zamir, D. and Tanksley, S. 1998. Advanced backcross QTL analysis in tomato. Identification of QTLs for traits of agronomic importance from *Lycopersicon hirsutum*. Theor. Appl. Genet. 97:381–397).

SUMMARY OF THE INVENTION

The present invention seeks to provide a method for breeding tomatoes having fruit that naturally dehydrate while still attached to the tomato plant and thus have a reduced water content, and to tomatoes having reduced water content and to products of the method.

The development of tomato varieties with the trait of naturally dehydrating while still attached to the vine, without the accompaniment of degradative processes leading to fruit breakdown is highly valuable to the various components of the tomato industry. It can contribute to reduction of processing costs and energy expenditures in the production of pastes, sauces and ketchups. It can contribute to the production of high quality dried and semi-dried (raisin-type) tomato products. It can contribute to the improvement of tomato fruit transport since the volume of transported material will be decreased. It can improve the storage ability of the tomato fruit since reduced water content will be accompanied by increased soluble solids concentration which contributes to the resistance to microbial spoilage.

There is thus provided in accordance with a preferred embodiment of the present invention a method for breeding tomato plants that produce tomatoes with reduced fruit water content including the steps of crossing at least one *Lycopersicon esculentum* plant with a *Lycopersicon* spp. to produce hybrid seed, collecting the first generation of hybrid seeds, growing plants from the first generation of hybrid seeds, pollinating the plants of the most recent hybrid generation, collecting the seeds produced by the most recent hybrid generation, growing plants from the seeds of the most recent hybrid generation, allowing plants to remain on the vine past the point of normal ripening, and screening for reduced fruit water content as indicated by extended preservation of the ripe fruit and wrinkling of the fruit skin.

In accordance with a preferred embodiment of the present invention the steps of pollinating, collecting the seeds, and growing plants are repeated at least once.

Further in accordance with a preferred embodiment of the present invention the step of pollinating includes self pollination.

Still further in accordance with a preferred embodiment of the present invention the step of pollination includes back crossing with a *Lycopersicon esculentum* plant.

Additionally in accordance with a preferred embodiment of the present invention the *Lycopersicon* spp plant is a *Lycopersicon hirsutum* plant.

In accordance with a preferred embodiment of the present invention the method additionally includes the steps of crossing plants derived from hybrid seeds whose progeny show reduced fruit water content with a *Lycopersicon* plant, growing the crossed plants, and selecting plants with tomato fruits having an increased dry weight percentage as compared to fruit from a non-crossed *Lycopersicon*. The steps of crossing and selecting may be repeated at least once. The crossing may include sexual or asexual crossing. The asexual crossing may include somatic cell hybridization.

Further in accordance with a preferred embodiment of the present invention the method additionally includes the step of propagating the plants with tomato fruits having the desired characteristics. The step of propagating may include vegetative propagation or propagation by seed.

In accordance with a preferred embodiment of the present invention the method additionally includes the steps of crossing plants derived from hybrid seeds whose progeny show reduced fruit water content with a *Lycopersicon* plant, growing the crossed plants, harvesting ripe tomato fruits before signs of dehydration thereof, and allowing the fruits to dehydrate after removal from the plant.

There is also provided in accordance with a preferred embodiment of the present invention a tomato fruit characterized by a capability of natural dehydration while on a tomato plant, natural dehydration being defined as wrinkling of skin of the tomato fruit when the fruit is allowed to remain on the plant after a normal ripe harvest stage, the natural dehydration being generally unaccompanied by microbial spoilage.

There is also provided in accordance with a preferred embodiment of the present invention a tomato fruit characterized by an untreated skin which permits hydration of the fruit so as to obtain wrinkling of the skin, the dehydration being generally unaccompanied by microbial spoilage.

DETAILED DESCRIPTION OF PREFERRED EMBODIMENTS

Reference is now made to a method for breeding tomatoes having fruit that naturally dehydrate while still attached to the tomato plant and reduced water content.

The method for breeding tomato plants includes first hybridizing at least one *Lycopersicon esculentum* plant with a wild *Lycopersicon* spp. plant. The fruits of the *L. esculentum* plants are then allowed to ripen and the hybrid ($F_1$) seeds are collected. The collected $F_1$ seeds are then planted and $F_1$ plants are grown and allowed to self-pollinate. Selfing may be continued for at least one additional generation or the F1 plants may be crossed to a *L. esculentum* parental plant. Fruits from selfed or backcrossed generations are allowed to remain on the vine past the point of normal ripening, as determined by change of fruit color, and screened for the presence of natural dehydration. Natural dehydration, or reduced water content, is indicated by the wrinkling of the fruit skin when the fruit is allowed to remain on the vine after the normal red ripe harvest stage.

Plants from any of the selfed generations may be propagated for use by vegetative propagation methods such as micropropagation or by sexual propagation methods. The plants may also be crossed with other *L. esculentum* cultivars to create varieties that incorporate characteristics other than reduced fruit water content. The varieties may then be propagated by vegetative or sexual propagation methods.

Plants from any of the selfed generations may also be back crossed to *L. esculentum* for at least one generation. The fruits of the last back cross generation are allowed to remain on the vine past the normal point of ripening. The appearance of dehydration as evidenced by wrinkling of the fruit skin indicates reduced water content in the fruit. Plants selected for this trait may then be propagated either vegetatively or by seed based propagation. Selected plants may then also be crossed with other *L. esculentum* cultivars to create varieties that incorporate characteristics other than reduced fruit water content. The varieties may then also be propagated by vegetative or sexual propagation methods.

Reference is now made to the following example that illustrates the invention.

EXAMPLE 1

Plants of the *L. esculentum* breeding line 1630 (a Volcani Institute male sterile breeding line, used to simplify the production of the interspecific hybrid) were pollinated with pollen of the wild species *L. hirsutum* (LA1777). Hybrid F1 plants were grown and allowed to self-pollinate, generating F2 seed. F2 seed were sown and about 350 plants were grown in a screenhouse and allowed to self-pollinate. Ripe fruit from each individual plant that produced fruit were individually analyzed for soluble solids (refractometrically) to insure the lines also included the characteristic of high soluble solids. Only 25 of the interspecific F2 plants freely produced fruit. Three F2 plants were selected based on their high sugar content (Brix in excess of 10) when ripe. For example, fruit of F2-82 had 71 mg soluble sugar, composed of sucrose, glucose and fructose, per gram fresh weight of fruit, as determined by the method described herein below. F3 seeds were sown and ten plants of each of the F3 plants of these three F2 selections (termed F2-24, F2-82 and F2-134) were grown, and fruit was allowed to remain on the vine past the normal stage of ripening and harvest. Fruit from these F3 plants were generally yellow when ripe and did not turn red even after the normal ripening stage. Among the F3 plants one plant (F3-203-10, derived from F2-134) showed the characteristic of signs of fruit dehydration, evidenced by wrinkling of the fruit skin.

A pedigree breeding program was developed to obtain tomatoes with reduced water content using as a selection system signs of fruit dehydration as evidenced by wrinkling of the fruit skin after the red ripe stage. This breeding strategy consisted of selfing F3-203-10 until the F4 generation and backcrossing to L. esculentum breeding line L-27, with the product of this cross being selfed for four additional generations to produce the BC1F4 population. Lines of this population (lines 901 and 903) as well as hybrid plants derived from crosses between this population and commercial tomato cultivars (cv. F139 and cv. BR124) produced plants that all showed the trait of fruit dehydration as evidenced by wrinkling of the ripe fruit skin. The presence of the trait in the hybrid plants indicates that the trait is heritable, governed by dominant genetic factors, and can be selected for in the early generations of the breeding program.

EXAMPLE 2

Pollen from one plant (F2-82) which was characterized by high soluble sugar level in the mature fruit (71 mg soluble sugar, composed of sucrose, glucose and fructose, per gram fresh weight of fruit) was used to pollinate two standard, industry type tomatoes (breeding lines A701 and 699) for the production of two backcross-F1 (BC-F1) populations. One-hundred BC-F2 plants from each of the two hybrids were grown and the presence of signs of fruit dehydration, evidenced by wrinkling of the fruit skin, were seen in fruit of plants from these F2 populations. This shows that even at early stages of a selection program, the trait can be selected for without large populations of plants.

Experiment 3

Fruit of progeny of advanced lines derived from the lines described in experiment 1, that showed the characteristic to dehydrate on the vine, as evidenced by the wrinkling of the fruit were harvested and the juice pressed and Brix of the expressed juice was measured by a digital refractometer (Atago model X-1). The following table shows characteristic Brix values of some of the partially wrinkled but not fully dehydrated. The results of this experiment indicate that the trait of fruit dehydration and increase in Brix value is a selectable inherited trait. The parental selection (self of 1465-3) was partially dehydrated as was the F1 hybrid between 1465-3 and the cherry cultivar F139. This indicates that the trait is at least partially dominant in its inheritance pattern. Similarly, 3 representative plant selections from the F2 population (1730) derived from the self of the F1 (1465-3×F139) which showed the trait of fruit wrinkling are presented and indicates that the selection method can be used in the segregating F2 population.

TABLE 1

Brix values of partially dehydrated tomato fruit, harvested from the vine at the stage when fruit wrinkling was visually observable. Fruit size was of the cherry-tomato size (approx. 10–15 gr).

| tomato plant | cross | generation | Brix |
| --- | --- | --- | --- |
| 1630-1 + 2 | 1465-3 self | BC2F2 | 19.2 |
| 1631-1 | 1465-3 × cv.139 | BC3F1 | 17.4 |
| 1730-3 | 1631-2 self | BC3F2 | 22.4 |
| 1730-4 | 1631-2 self | BC3F2 | 29.0 |
| 1730-5 | 1631-2 self | BC3F2 | 11.1 |

Experiment 4

In an experiment to determine whether the dehydration process can take place after removal from the vine, red ripe fruits from a BCF3 population were harvested, as above, and allowed to remain and dehydrate on netted screens on the laboratory bench without temperature control. After approximately one month the fruit had reached 86.2% dry weight, and were generally unaccompanied by microbial spoilage. Percent dry weight was calculated as the percentage of weight after drying in a forced air oven at 60° C. for 24 overnight, compared to the weight of fruit prior to oven drying. Ten representative fruit were used to calculate the percent dry weight.

Such fruit has been maintained for over a year at 5° C. and at room temperature in an uncontrolled environment for at least 5 months, without further decay. The results of these experiments indicate that the dehydrated fruit may be harvested at various stages of dehydration (even before dehydration commences) and that dehydration of the fruit may also continue after detachment from the vine.

Experiment 5

In order to characterize the development of the dehydration process an experiment was carried out in which 14 red-ripe fruit from plants which showed the trait of dehydration of the fruit, but which themselves had not yet reached the dehydration stage, were selected. Seven of these fruit were harvested when red-ripe and analyzed immediately, as described below. The other seven fruit were allowed to remain attached to the vine for an additional 14 days and, when fruit wrinkling was observed, were analyzed, as follows.

Each fruit was individually weighed, a sample of the fruit juice was tested by refractometer, for Brix value. An additional sample of each fruit was weighed fresh and then dried in an oven, as described above, for the calculation of percent dry weight. A third portion of each fruit was used for the analysis of individual soluble sugar levels, as follows.

Individual fruits were harvested and a portion of the fruit pericarp was placed in 80% ethyl alcohol and heated to 70° C. in order to stop enzymatic activity and extract the soluble sugars. Soluble sugars were extracted three times in successive changes of 80% alcohol which was then evaporated.

The sugars were then dissolved in double distilled water, centrifuged at 5,000 rpm in an eppendorf centrifuge tube for 15 minutes to remove cell debris and 0.5 ml aliquot passed through a 0.45 micron filter in preparation for high Pressure Liquid Chromatography (HPLC) analysis. HPLC analysis was performed using a BioRad (Richmond, Calif., USA) Fast Carbohydrate column for the separation of glucose, fructose and sucrose according to the manufacturer's instructions. The sugars were identified and quantified according to chromatographic behavior of standards for the sugars which were obtained from Sigma (St. Louis, Mo., USA).

The results of this study are shown in Table 2 and show that the wrinkling phenomenon is accompanied by loss of water from the fruit, leading to an increase in % dry weight, an increases in Brix and individual sugar concentrations. The dry matter per fruit remains approximately the same. This indicated that the phenomenon of fruit wrinkling, and the concomitant increase in sugar concentration and in dry matter concentration is primarily one of natural dehydration of the fruit, without a concomitant loss of fruit dry matter content.

TABLE 2

| Trait | Red ripe | Wrinkled |
| --- | --- | --- |
| Fresh weight (g/fruit) | 16.63 | 12.20 |
| Percent dry weight | 12.53 | 17.89 |
| Brix | 11.51 | 14.57 |
| Sugars (mg/gm fr w) | | |
| Total | 66.4 | 86.4 |
| Sucrose | 3.8 | 6.1 |
| Glucose | 30.5 | 38.4 |
| Fructose | 32.1 | 41.9 |
| Water content (g/fruit) | 14.55 | 10.02 |
| Dry weight (g/fruit) | 2.08 | 2.18 |
| Sugars (g/fruit) | 1.10 | 1.05 |

In summary, with the methods of the present invention, a tomato fruit can be obtained characterized by an untreated skin which permits dehydration of the fruit so as to obtain wrinkling of the skin, wherein the dehydration is generally unaccompanied by microbial spoilage. In another aspect of the invention, a tomato fruit can be obtained characterized by a capability of natural dehydration while on a tomato plant, natural dehydration being defined as wrinkling of skin of the tomato fruit when the fruit is allowed to remain on the plant after a normal ripe harvest stage, wherein the natural dehydration is generally unaccompanied by microbial spoilage.

Alternatively, it is noted that the tomato fruit can be treated with a substance, such as sulfur dioxide, to help retain skin color during and after dehydration, such as is done with dried fruits such as raisins.

It will be appreciated by persons skilled in the art that the present invention is not limited to what has been particularly shown and described herein above. Rather the scope of the present invention is defined only by the claims which follow:

What is claimed is:

1. A method of producing tomato fruit capable of natural dehydration comprising:
    (a) crossing at least one *Lycopersicon esculentum* plant with a *Lycopersicon hirsutum* to produce hybrid plants; and subsequently;
    (b) self-crossing and/or back-crossing said hybrid plants of step (a); and subsequently
    (c) growing said hybrid plants of step (b) such that the fruit remains on the vine of said hybrid plants past normal red ripe harvest stage; and subsequently
    (d) screening said hybrid plants of step (c) and isolating plants having fruit exhibiting a wrinkling phenotype, thereby producing tomato fruit capable of natural dehydration.

2. The method according to claim 1, wherein step (a) is effected by pollinating, collecting the seeds, and growing said hybrid plants.

3. The method according to claim 1, further comprising harvesting said tomato fruit following fruit wrinkling.

4. An isolated whole tomato fruit comprising a genome of the *Lycopersicon esculentum* species, wherein said genome comprises an introgression from *Lycopersicon hirsutum*, said introgression allowing natural fruit dehydration which results in skin wrinkling of the tomato fruit.

5. An isolated whole tomato fruit comprising a genome of the *Lycopersicon esculentum* species, wherein said genome comprises an introgression from *Lycopersicon hirsutum*, said introgression causing untreated skin wrinkling of the tomato fruit.

* * * * *